US00PP10211P

United States Patent [19]

Pieters

[11] Patent Number: Plant 10,211

[45] Date of Patent: Jan. 27, 1998

[54] CHRYSANTHEMUM PLANT NAMED 'ALCALA'

[76] Inventor: Dirk Pieters, Schierveldestraat 3A, Oosnieuwkerke, 8840 Staden, Belgium

[21] Appl. No.: 755,402

[22] Filed: Nov. 21, 1996

[51] Int. Cl.[6] ..... A01H 5/00

[52] U.S. Cl. ..... Plt./74.1

[58] Field of Search ..... Plt./74.1, 84.5

*Primary Examiner*—Howard J. Locker

*Attorney, Agent, or Firm*—C. A. Whealy

[57] ABSTRACT

A distinct cultivar of Chrysanthemum plant named 'Alcala', characterized by its spherical and mounded plant habit; high vigor and rapid growth rate; multiple secondary laterals and numerous leaves; daisy-type inflorescences; purple ray florets with yellow disc florets; numerous inflorescences per plant; and good garden performance.

2 Drawing Sheets

The present invention relates to a new and distinct cultivar of garden Chrysanthemum plant, botanically known as *Dendranthema grandiflora* and referred to by the cultivar name Alcala.

The new cultivar is a product of a planned breeding program conducted by the inventor in Staden, Belgium. The objective of the breeding program was to create new garden Chrysanthemum cultivars that are freely branching and have numerous and long-lasting inflorescences.

The new cultivar originated from a cross made by the inventor of the nonpatented cultivar Rostoline as the female, or seed, parent with the nonpatented cultivar Prisma as the male, or pollen, parent.

The new Chrysanthemum was discovered and selected by the inventor as a flowering plant within the progeny of the stated cross in a controlled environment in Staden, Belgium.

Asexual reproduction of the new cultivar by terminal cuttings taken at Staden, Belgium, has shown that the unique features of this new Chrysanthemum are stable and reproduced true to type in successive generations.

The following traits have been repeatedly observed and are determined to be the unique characteristics of 'Alcala'. These characteristics in combination distinguish 'Alcala' as a new and distinct cultivar:

1. Spherical and mounded plant habit, vigorous, and rapid growth rate.
2. Extremely freely branching with secondary laterals and numerous leaves gives full, bushy appearance.
3. Daisy-type inflorescences.
4. Purple ray florets with yellow disc florets.
5. Numerous inflorescences per plant.
6. Good garden performance.

The cultivar Alcala has not been observed under all possible environmental conditions. The phenotype may vary somewhat with variations in environment such as temperature, daylength and light intensity, without, however, any variance in genotype.

In side-by-side comparisons in Staden, Belgium, under commercial practice, plants of the new Chrysanthemum differ from plants of the female parent, the cultivar Rostoline, in ray floret color, inflorescence form and size. In the same comparisons, plants of the new Chrysanthemum differ from the male parent, the cultivar Prisma, in ray floret color, inflorescence form and plant size.

Plants of the new Chrysanthemum can be compared to the cultivar Stargazer (U.S. Plant Pat. No. 5,695). However, in side-by-side comparisons conducted in Oxnard, Calif., under commercial practice, plants of the new Chrysanthemum differed from plants of the cultivar Stargazer in the following characteristics:

1. Plants of the new Chrysanthemum are full, spherical and mounding whereas plants of the cultivar Stargazer are upright.
2. Plants of the new Chrysanthemum are more vigorous than plants of the cultivar Stargazer.
3. Plants of the new Chrysanthemum are more freely branching with almost twice the number of primary laterals of plants of the cultivar Stargazer. In addition, plants of the new Chrysanthemum have numerous secondary lateral branches.
4. Leaves of plants of the new Chrysanthemum are smaller but more numerous than leaves of plants of the cultivar Stargazer.
5. Inflorescences of plants of the new Chrysanthemum are smaller, flatter and have fewer ray florets but are more numerous than inflorescences of plants of the cultivar Stargazer.
6. Plants of the new Chrysanthemum have weaker and shorter peduncles than plants of the cultivar Stargazer.

A detailed comparison of plants of the new Chrysanthemum and the cultivar Stargazer appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Alcala' with five cuttings in the container.

The second photograph comprises a close-up view of leaves at different stages of development and a fully opened inflorescences. Foliage and floret colors in the photographs may appear different from the actual colors due to light reflectance.

In the following description, color references are made to the Royal Horticultural Society Colour Chart except where general terms of ordinary dictionary significance are used. The following observations and measurements describe plants grown in Oxnard, Calif., under commercial practice in a glass-covered greenhouse with night temperatures ranging between 14 and 20C, day temperatures ranging between 20 and 30C, and average light levels of 5,000 to 6,000 footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Alcala.

Commercial classification: Garden chrysanthemum.

Parentage:

*Female, or seed, parent.*—*Dendranthema grandiflora* cultivar Rostoline (not patented).

*Male, or pollen, parent.*—*Dendranthema grandiflora* cultivar Prisma (not patented).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Spherical and mounded growth habit. Rapid growth rate and vigorous. Extremely freely branching with numerous secondary laterals.

*Plant height.*—About 20 cm.

*Lateral branch length.*—About 14 cm.

*Quantity of lateral branches after removal of apical meristem.*—Primary laterals: About 6. Secondary laterals: About 14.

*Stem color.*—38B.

*Foliage description.*—Number of leaves per plant: About 168. Number of leaves per lateral branch: Primary laterals: About 14. Secondary laterals: About 15. Leaf arrangement: Alternate. Leaf size, fully expanded: Length: About 3.8 cm. Width: About 2.7 cm. Leaf apex: Rounded, apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 8 mm. Color: Young foliage adaxial surface: 147A. Young foliage abaxial surface: 147B. Fully expanded foliage adaxial surface: 147A. Fully expanded foliage abaxial surface: 147B. Venation adaxial surface: 138A. Venation abaxial surface: 147C. Petiole: 147A.

Inflorescence description:

*Appearance.*—Daisy-type inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 49 days later. Inflorescences maintain good substance for three weeks under bright natural daylight.

*Quantity of Inflorescences.*—About 12 to 14 inflorescences per flowering stem.

*Inflorescence size.*—Diameter: About 4 cm. Depth (height): About 8 mm Diameter of disc: About 8 mm.

*Opening inflorescences.*—Bud shape: Spherical. Bud size: Length: About 6 mm. Width: About 5 mm. Bud color: 75A.

*Ray florets.*—Shape: Narrow, oblong. Size: Length: About 2 cm. Width: About 4 mm. Apex: Slightly tri-dentate. Base: Acute. Margin: Entire. Texture: Matte, soft, smooth and glabrous. Aspect: Flat, but reflex rapidly with development. Number of ray florets per inflorescence: About 28. Color: When opening, adaxial surface: 72A. When opening, abaxial surface: 84B. Mature, adaxial surface: 80C. Mature, adaxial surface: 84C Fading to: 78C.

*Disc florets.*—Shape: Tubular. Size: Length; About 4 mm. Width: About 1 min. Number of disc florets per inflorescence: About 90. Color: Immature: 4C. Mature: 4B.

*Peduncle.*—Aspect: Weak, wiry and angled about 20° to 25° to the stem. Length: First peduncle: About 4.7 cm. Fourth peduncle: About 5.8 cm. Texture: Pubescent. Color: 138B.

*Reproductive Organs.*—Androecium: Present on disc florets only. Anther color: 13A. Pollen: Moderate, 13A in color. Gynoecium: Present on both ray and disc florets. Style color: 154C.

Disease resistance: No known Chrysanthemum diseases observed to date on plants grown under commercial greenhouse conditions.

Seed production: Seed production has not been observed.

CHART A

| CHARACTERISTIC | 'ALCALA' | 'STARGAZER' |
|---|---|---|
| PLANT SHAPE | Spherical, rounded | Upright |
| GROWTH HABIT | Medium to short | Medium |
| GROWTH RATE/VIGOR | Rapid/vigorous | Moderate/ moderate |
| PLANT HEIGHT | About 20 cm | About 24 cm |
| LATERAL STEM LENGTH | About 14 cm | About 18 cm |
| QUANTITY OF LATERAL BRANCHES AFTER PINCHING | About 6 primary laterals with about 14 secondary laterals | About 3 to 4 |
| STEM COLOR | 138B | 144A |
| LEAF LENGTH | About 3.8 cm | About 5 cm |
| LEAF WIDTH | About 2.7 cm | About 3.8 cm |
| PETIOLE LENGTH | About 8 mm | About 1.8 cm |
| QUANTITY OF INFLORESCENCES PER LATERAL STEM | About 12 to 14 | About 7 to 8 |
| INFLORESCENCE DIAMETER | About 4 cm | About 5 cm |
| INFLORESCENCE HEIGHT | About 8 mm | About 1.2 cm |
| BUD COLOR | 75A | 72A |
| RAY FLORET SHAPE | Narrow, oblong | Broad, obovate |
| RAY FLORET LENGTH | About 2 cm | About 2.2 cm |
| RAY FLORET WIDTH | About 4 mm | About 7 mm |
| RAY FLORET COLOR, WHEN OPENING, ADAXIAL | 72A | 64A |
| RAY FLORET COLOR, WHEN OPENING, ABAXIAL | 84B | 64B |
| RAY FLORET COLOR, MATURE, ADAXIAL | 80C | 70B |
| RAY FLORET COLOR, MATURE, ABAXIAL | 84C | 75C |
| RAY FLORET COLOR FADING TO | 78C | 70C |
| NUMBER OF RAY FLORETS PER INFLORESCENCE | About 28 | About 60 |
| DISC FLORET COLOR, IMMATURE | 4C | 2C |
| DISC FLORET COLOR, MATURE | 4B | 2C |
| DIAMETER OF DISC | About 8 mm | About 1 cm |
| NUMBER OF DISC FLORETS PER INFLORESCENCE | About 90 | About 114 |
| PEDUNCLE STRENGTH | Weak, wiry | Strong |
| PEDUNCLE LENGTH, FIRST | About 4.7 cm | About 6.2 cm |
| PEDUNCLE LENGTH, FOURTH | About 5.8 cm | About 8.5 cm |
| PEDUNCLE COLOR | 138B | 146C |
| ANTHER COLOR | 13A | 12A |
| POLLEN COLOR | 13A | 12A |

It is claimed:

1. A new and distinct cultivar of Chrysanthemum plant named 'Alcala', as illustrated and described.

* * * * *

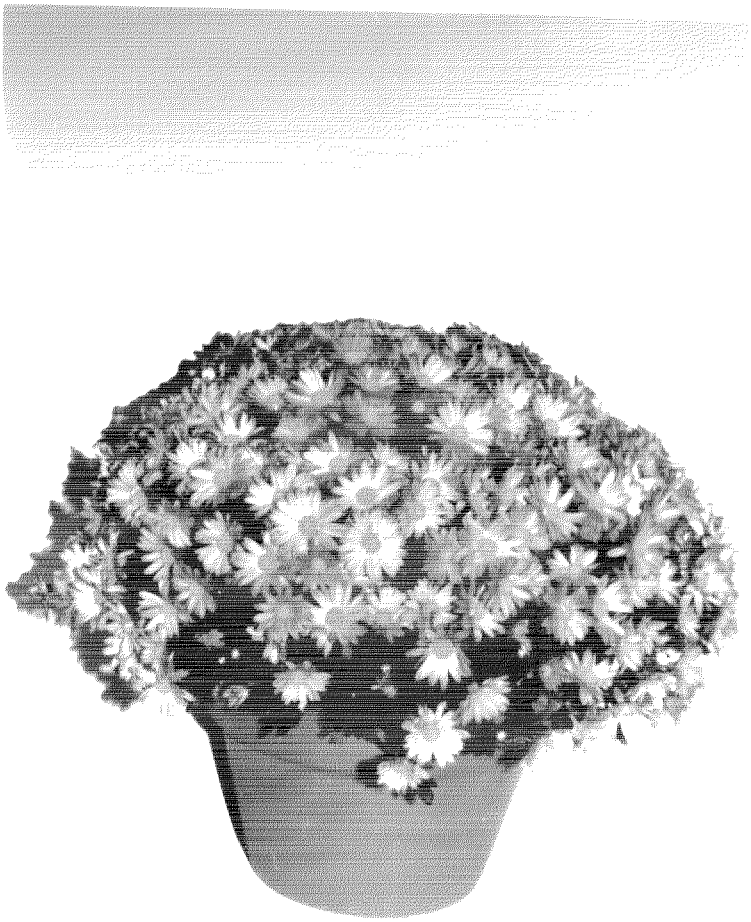

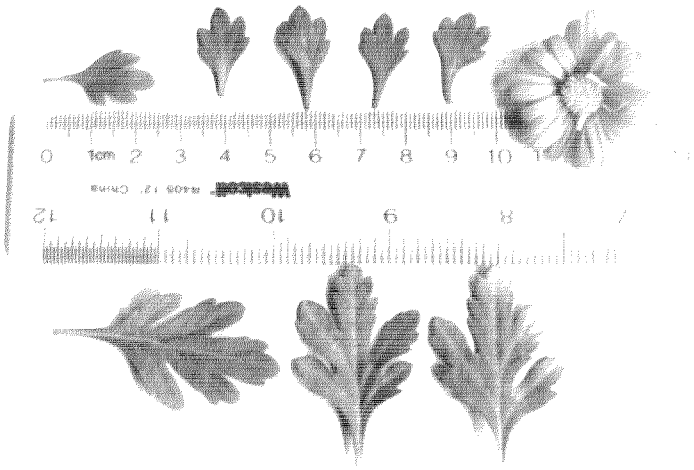
12
11
10
9
8
7
1cm
0
2
3
4
5
6
7
8
9
10

UNITED STATES PATENT AND TRADEMARK OFFICE

CERTIFICATE OF CORRECTION

PATENT NO. : Plant 10,211
DATED : January 27, 1998
INVENTOR(S) : Dirk Pieters

It is certified that error appears in the above-indentified patent and that said Letters Patent is hereby corrected as shown below:

Column 2, line 31, change "inflorescences" to -- inflorescence --.
Column 3, line 22, change "38B" to -- 138B --.
Column 4, line 2, change "About 1 min." to -- About 1 mm --.

Signed and Sealed this

Second Day of February, 1999

*Attest:*

*Attesting Officer*

*Acting Commissioner of Patents and Trademarks*